United States Patent
Easter et al.

(10) Patent No.: US 6,293,847 B1
(45) Date of Patent: Sep. 25, 2001

(54) APPARATUS FOR CHEMICAL MECHANICAL POLISHING ENDPOINT DETECTION USING A HYDROGEN SENSOR

(75) Inventors: William Graham Easter; John Albert Maze; Frank Miceli; Sudhanshu Misra; Allen Yen, all of Orlando, FL (US)

(73) Assignee: Agere Systems Guardian Corp., Allentown, PA (US)

( * ) Notice: Subject to any disclaimer, the term of this patent is extended or adjusted under 35 U.S.C. 154(b) by 0 days.

(21) Appl. No.: 09/418,087

(22) Filed: Oct. 14, 1999

(51) Int. Cl.[7] .................................................. B24B 51/00
(52) U.S. Cl. ................................................. 451/8; 451/288
(58) Field of Search .......................... 451/3, 8, 41, 285, 451/286, 287, 288, 289, 290

(56) References Cited

U.S. PATENT DOCUMENTS 5,668,301 * 9/1997 Hunter .................................. 73/23.2

OTHER PUBLICATIONS

Lundström et al. "A Hydrogen–Sensitive Pd–Gate MOS Transistor" *Journal of Applied Physics* vol. 46, No. 9, Sep. 1975, pp. 3876–3881.

Ito & Ohgami, "Hydrogen Detection Based on Coloration of Anodic Tungsten Oxide Film", *Applied Physics Letters*, vol. 60, No. 8, Feb. 24, 1992, pp. 938–940.

* cited by examiner

*Primary Examiner*—Timothy V. Eley
(74) *Attorney, Agent, or Firm*—Christie, Parker & Hale, LLP

(57) ABSTRACT

An apparatus for determining endpoint in the chemical mechanical polishing of a metal film using an acidic slurry includes a hydrogen sensor which senses the amount of hydrogen vapor being produced as a result of the reaction between the metal film and the acidic slurry. When the concentration of hydrogen vapor in the reaction area drops, endpoint is attained and the polishing operation may be terminated or otherwise adjusted. Hydrogen sensing elements include a palladium gate MOS transistor, expandable plastics and a tungsten oxide film.

18 Claims, 2 Drawing Sheets

APPARATUS FOR CHEMICAL MECHANICAL POLISHING ENDPOINT DETECTION USING A HYDROGEN SENSOR

FIELD OF THE INVENTION

The present invention relates generally to chemical mechanical polishing of substrates, and more particularly to an apparatus for detecting a polishing endpoint by sensing hydrogen vapor produced by a reaction between metal material being polished and an acidic polishing slurry.

BACKGROUND OF THE INVENTION

Chemical mechanical polishing (CMP) is one method of providing a planarized substrate surface. Such substrates are used in the manufacture of integrated circuit devices. CMP may be used to planarize raw substrates or to completely or partially remove a bulk deposited layer, but more is commonly used to planarize a surface by partially removing layers which have been deposited over non-planar features formed in or on a subjacent layer. A typical CMP apparatus employs a rotating polishing surface, such as a consumable polishing pad, against which the surface of the substrate being polished is placed. The CMP apparatus also includes a carrier which secures the substrate in a desired position with respect to the pad. The carrier includes means for providing a force to keep the substrate in contact with the pad, and also may include means for rotating, vibrating, or oscillating the substrate. During polishing, a slurry having both chemical and abrasive agents is supplied to the interface between the substrate and the pad, to enhance the rate at which material is removed from the substrate. The chemical agents included in the slurry are generally chosen to be reactive towards the material being removed by polishing. For example, when a metal material is being polished, the polishing slurry will be acidic in nature.

One problem associated with CMP is endpoint detection. Endpoint may be defined as the point at which the desired polishing operation is completed. When "endpoint" is attained, a number of different actions may be taken in response. For example, the entire polishing process may be terminated when endpoint is attained or the polishing conditions may be changed as the polishing process continues, with another polishing operation, to polish an underlying film. It can be seen that a substrate containing a stack of films to be polished, may include a number of discrete polishing operations, each of which includes an associated "endpoint".

Depending on the chemical mechanical polishing operation being performed, "endpoint" may signify different events. For example, when polishing a raw substrate, the "endpoint" condition may be attained when a certain predetermined substrate thickness has been removed. The same is true for a layer or film which is being partially removed. When a film is being completely removed from a substrate, "endpoint" is attained upon complete removal of the film. When CMP is used to planarize a substrate by removing portions of a film which extend above non-planar underlying features, "endpoint" is achieved when the surface is essentially planar. Generally speaking, an "endpoint" condition is attained after a predictable amount of material has been removed from the surface. It is therefore necessary to accurately detect when endpoint is achieved so that the polishing operation may be quickly terminated or otherwise adjusted at that point. Because the substrate is polished face-down and the polishing surface is generally contiguous with the polishing pad, a process monitor cannot easily be used to view the progress of the polishing operation, especially by directly monitoring the surface being polished. As such, it is difficult to attempt to use such a monitor to determine the polishing "endpoint".

Variations in the polishing conditions also impede an accurate determination of the polishing endpoint. For example, variations in the slurry composition, pad condition, relative speed between the pad and the substrate, the material being polished, and the load of the substrate on the pad, cause variations in the material removal rate. These variations in the material removal rate cause variations in the time needed to reach the polishing endpoint. Therefore, the polishing endpoint cannot reliably be estimated merely as a function of polishing time.

A common application of CMP is to partially or completely remove a deposited metal material from a substrate by polishing. One such example is to planarize a substrate surface using damascene technology. In damascene technology, trenches, grooves or other openings may be formed within a subjacent layer such as a dielectric film formed over a substrate. Next, a bulk deposited layer, generally a conductive material such as metal, is formed over the upper surface of the subjacent layer and within the openings which extend down into the subjacent layer. One aspect of CMP is to remove the bulk of the deposited metal layer from over the upper surface of the subjacent layer, leaving areas of the metal layer only in the openings formed within the subjacent layer. In this manner, a wiring pattern is produced. It can be understood that it is desirable to terminate the polishing operation when endpoint is achieved, i.e. when the bulk of the deposited metal layer is removed from over the upper surface of the subjacent layer, but remains within the openings so that the remaining portions of the metal layer form a substantially planar surface with the upper surface of the subjacent layer.

One general approach to predicting the polishing endpoint is to remove the substrate from the polishing surface and measure the thickness of the substrate or the film being removed by polishing. By periodically removing the substrate from the polishing apparatus and measuring its thickness, the quantity of material being removed from the substrate may be determined. As such, a linear approximation of the material removal rate may be used to determine the polishing endpoint. This technique is time consuming, however, and does not account for sudden changes in the removal rate that may occur between measurement intervals, or for other variations in the material removal rate as discussed above.

Several other non-invasive techniques for endpoint detection are known. These techniques generally fall into two categories: those which require access to the surface of the substrate being polished, and those which determine the polishing endpoint by determining changes in the operating conditions of the polishing apparatus.

Techniques included within first category typically require real-time access to at least a portion of the substrate surface being polished, such as by sliding a portion of the substrate over the edge of the polishing pad and simultaneously analyzing the exposed portion of the substrate. For example, where polishing is used to remove the bulk of a conductive film such as a metal, and to form metal lines embedded within trenches formed in a subjacent dielectric layer as in the planarization example discussed above, the overall or composite reflectivity of the surface being polished changes as the metal film is removed and the dielectric layer is exposed. By monitoring the reflectivity of the polished surface or the wavelength of light reflected from the surface, the polishing endpoint can be detected as the reflectivity changes when the dielectric layer is exposed. However, this technique does not provide a way of determining the polishing endpoint unless an underlying layer such as the dielectric, is exposed during polishing and has a reflectivity which varies from the film being polished. Additionally, it is somewhat erratic in predicting the polishing endpoint unless all of the underlying surface of a different reflectivity, is simultaneously exposed. Furthermore, the detection apparatus is delicate and subject to frequent breakdown caused by the exposure of the measuring or detecting apparatus to the polishing slurry.

Another technique included within first category involves projecting a laser beam through an opening formed in the polishing pad, and onto the surface being polished. This technique is not favored because of the difficulty associated with projecting a laser through an opening which must be formed in an otherwise contiguous, rotating polishing pad. Additionally, the window, through which the laser beam is projected, must be kept clean. This is quite difficult to do, especially with some commonly used polishing slurries.

Techniques for determining the polishing endpoint included within is the second category, generally do so by monitoring various operating conditions of the polishing apparatus and indicating an endpoint condition when one or more of the operating conditions abruptly changes. An example of such an operating condition is the coefficient of friction at the interface of the polishing pad and the substrate. When a metal layer is being polished to expose an underlying dielectric layer, for example, the coefficient of friction will change when the dielectric layer is exposed. As the coefficient of friction changes, the torque necessary to provide the desired polishing pad speed also changes. By monitoring this change such as by monitoring the polishing motor current, endpoint may be detected. However, the coefficient of friction is a function of the slurry composition, the pad condition, the load of the substrate on the pad, and the surface condition of the substrate. In addition, the pad condition and the slurry composition at the pad-substrate interface changes as the substrate is being polished. Moreover, electrical noise may distort the characteristic being measured. Such effects may mask the exposure of the underlying dielectric layer (and removal of the bulk of the metal film), and they may prematurely endpoint the polishing operation. Additionally, using this method, the endpoint detection will work only if polishing is used to expose an underlying material having a frictional attribute different than that of the material being removed.

Another technique for determining endpoint included within the second category involves monitoring the power input to one or more of the polishing motors, such as the motor which rotates the polishing pad or a motor which may be used to rotate the substrate being polished. Using this technique, a determination that endpoint has been achieved, may be made when a pre-determined power sum is reached. Like the other techniques within the second category of endpointing techniques, this method also does not directly monitor physical activity occurring on the surface being polished during the polishing operation.

Therefore, none of the available endpointing techniques described above, detects endpoint by directly monitoring the film being removed, or other physical changes occurring on the surface being polished, without interrupting the polishing process. As such, none of the known techniques for determining endpoint, do so by actually sampling the surface during the polishing operation, and detecting that the bulk portion of the film being polished, is physically removed from the surface. It can be understood, then, that such a method and an apparatus for performing the same, are desirable in the art of CMP.

For the aspect of CMP directed to completely removing a metal layer or to forming conductive lines within trenches or the like using damascene techniques, endpoint is attained when the bulk of the metal material is removed from over the upper surface of the subjacent layer, but remains within the trenches to form a planar surface. In damascene applications, the metal film which remains within the trenches, produces a wiring pattern within the planar surface. At this point, it is desirable to terminate or otherwise adjust the polishing operation. Since the polishing slurry used to polish a metal material is acidic in nature and is therefore reactive towards the metal layer being polished, the polishing process produces reaction products such as hydrogen vapor. As such, when endpoint is achieved and the bulk of the metal layer is removed from over the substrate surface, the concentration of hydrogen vapor within the product stream, drops.

It can be seen that there is a need for an endpoint detection apparatus which can be used to detect endpoint at this point in order to terminate or otherwise adjust the polishing operation to avoid further undesired polishing.

SUMMARY OF THE INVENTION

The present invention relates to an endpoint detection system for use in conjunction with a chemical mechanical polishing operation. A metal layer is removed by polishing using an acidic slurry. A reaction between the metal layer being polished, and the acidic slurry, produces reaction products which include hydrogen vapor. A sample of the reaction products is sensed by a hydrogen sensor which includes a sensing element which may be a palladium gate transistor, a tungsten oxide film, or a plastic which expands when exposed to hydrogen vapor. The sensing element is oriented to be exposed to the reaction products.

Each sensing element includes a measurable characteristic which varies depending on the amount of hydrogen vapor present. When the bulk of the metal layer being polished, is removed, the amount of hydrogen vapor being produced, drops correspondingly. When this drop in hydrogen vapor concentration is detected by the sensor, the measurable characteristic changes and endpoint is thereby detected. At this point the polishing operation may be terminated or otherwise adjusted, responsive to the change in the amount of hydrogen vapor sensed.

DETAILED DESCRIPTION OF THE INVENTION

The present invention is directed to a system for determining the point at which endpoint is attained during a polishing operation used to polish a metal layer. The metal layer being polished may consist of aluminum, copper, tungsten, or other metals such as barrier materials. Examples of barrier materials are titanium, tantalum and other refractory metals. The metal material being polished may also be an aluminum alloy, a copper alloy, a tungsten alloy, or an alloy of another metal material. The metal layer being polished may consist of a metal material formed over a substrate, such as a semiconductor wafer commonly used in the semiconductor manufacturing industry. For example, the metal layer being polished may be a metal film formed directly on a substrate, or formed over another layer which is formed on the substrate. The metal layer being polished may represent a bulk film formed over a substantially planar substrate, and which is being completely removed. In another exemplary embodiment, the metal layer may represent a metal film formed over a subjacent layer and also within trenches, grooves, or other openings formed within the subjacent layer as in damascene processing.

Figure 1:
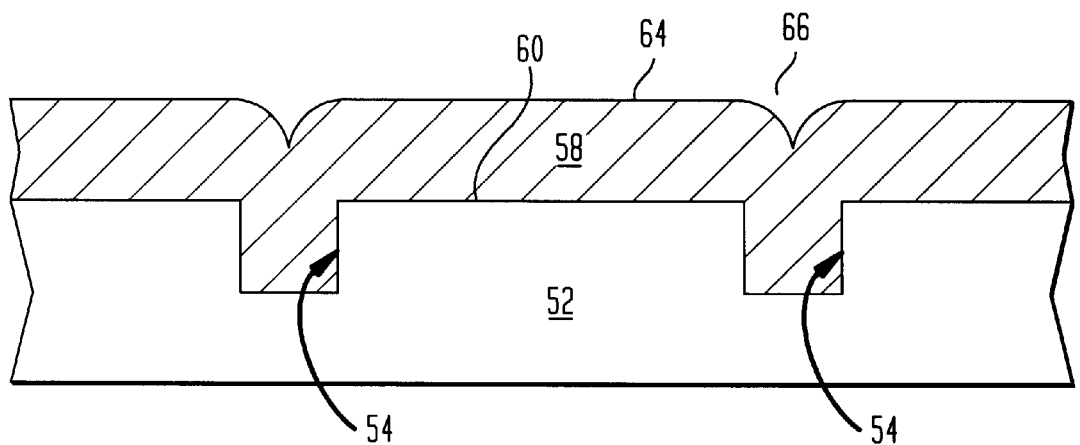
FIG. 1 is a cross-sectional view of a damascene structure ready to be polished.

FIG. 1 is a cross-sectional view showing a metal film formed over a subjacent layer using damascene processing techniques. In FIG. 1, subjacent layer 52 may be a substrate such as a silicon wafer, or it may be a dielectric, or other film formed over a substrate. Trenches 54 are formed within subjacent layer 52, and extend down from upper surface 60 of subjacent layer 52. It should be understood that trenches 54 are exemplary only: in other embodiments, they may take the shape of grooves, terraced trenches, or other openings formed within subjacent layer 52 and extending down from top surface 60. Hereinafter, the trenches, grooves, and other openings, will be referred collectively as "trenches". Metal layer 58 is formed over top surface 60 of subjacent layer 52, and within trenches 54. Metal layer 58 includes top surface 64. Metal layer 58 may include any of the metal materials described above, and may be formed using any suitable conventional method as available in the art.

It should be further understood that, according to common practice, many of the features shown in FIG. 1 have been expanded or reduced for clarity. As such, the features shown in FIG. 1 are not to scale. For example, trenches 54 are illustrated as being deeper and wider than in practice, and they are shown in closer proximity then as would be in practice. As such, it should be understood that the portion of metal layer 58 which is formed within trenches 54, is negligible when compared to the overall mass of metal film 58. The damascene structure shown in FIG. 1 is ready to be polished using chemical mechanical polishing methods.

Figure 2:
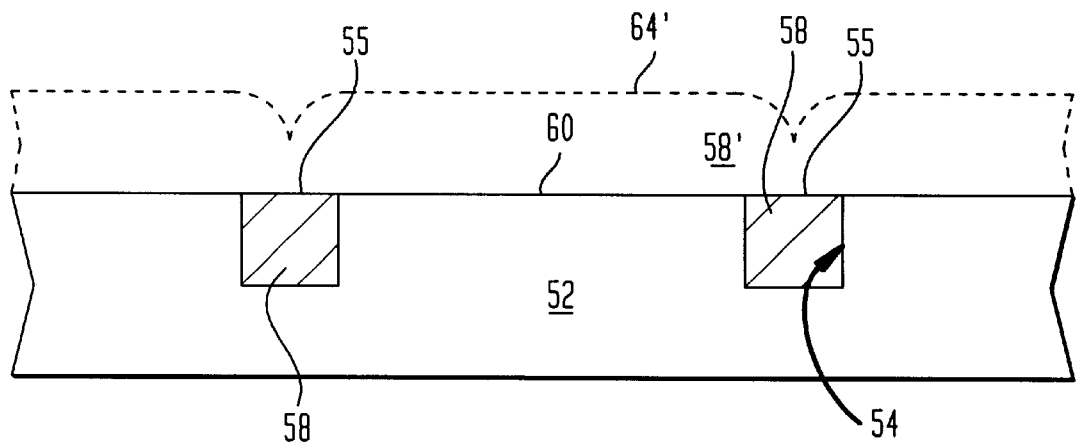
FIG. 2 is a cross-sectional view of the structure shown in FIG. 1, after the structure has been polished and an endpoint condition has been attained.

FIG. 2 shows the structure originally shown in FIG. 1, after a CMP operation has been used to remove the bulk portion of metal film 58. It can be seen that the portions of metal film 58 which had been formed over top surface 60, have been removed. (Ghost line 64' shows the initial upper surface of metal film 58' prior to the polishing operation.) It can be seen that top surfaces 55 of the filled trenches 54, together with top surface 60, form a substantially planar surface. As above, it should be noted that surfaces 55 are negligible in size when compared to the surface area of top surface 60 throughout the device being polished. In this manner it can be understood that the when the structure in FIG. 2 is attained during the polishing operation, all but negligible portions of the originally deposited metal is film 58, have been removed. It should be understood, however, that the portions of the metal film 58 which do remain in trenches 54, form a wiring structure within the device being formed. FIG. 2 therefore represents the point at which endpoint is attained for the polishing operation used to remove film 58 from over top surface 60, while allowing sections of metal film 58 to remain within trenches 54. At the point endpoint is attained, the amount of the metal film 58 being removed by the polishing operation, drops significantly. Once endpoint is attained, it may be desirable to completely terminate the polishing operation. Alternatively, it may be desirable to change at least some of the characteristics of the polishing operation and to continue to polish the surface which is newly exposed and includes top surface 60 and surface 55 of metal material 58 formed within trenches 54. An example of an adjustment made to the polishing process may be to adjust the characteristics of the polishing operation so as to produce a buffing process. This buffing process may be used to remove surface defects associated with the primary metal polishing operation.

Figure 3:
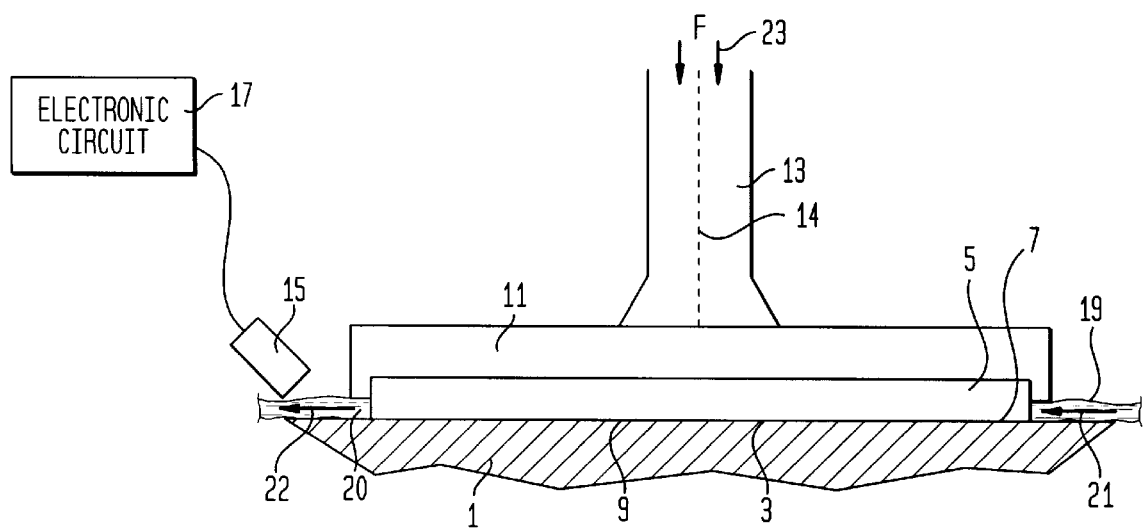
FIG. 3 is a side view of a chemical mechanical polishing operation.

FIG. 3 is a side view illustrating a CMP operation taking place. Polishing pad 1 includes pad surface 3. Substrate 5 which includes substrate surface 7 which is being polished, is secured by carrier 11. Carrier 11 is attached to shaft 13 which may be a spindle. In an exemplary CMP polishing operation, shaft 13 rotates about its axis 14 thereby rotating carrier 11 and substrate 5 which is secured within carrier 11. Also in the exemplary embodiment, translational motion is imparted upon polishing pad 1. In an exemplary embodiment, polishing pad 1 rotates about an axis other than axis 14 of shaft 13. As such, each of pad surface 3 of polishing pad 1, and substrate surface 7 of substrate 5 have translational motion along the plane formed by substrate surface 7. Substrate surface 7, which is being polished, is essentially in contact with pad surface 3 of polishing pad 1 to produce the polishing of substrate surface 7, and interface region 9 is thereby formed between the two surfaces 7, 3. During the polishing operation when each of the surfaces are being rotated respectively, a force "F" is applied along direction 23, thereby directing substrate surface 7 towards polishing pad 1, and producing contact between substrate surface 7 and pad surface 3.

As shown in FIGS. 1 and 2, substrate surface 7 of the substrate 5 being polished, includes a metal material which is being removed during the polishing operation. Characteristics of the polishing operation include the magnitude of force "F" applied along direction 23 to force the surfaces towards each other, the roughness of pad surface 3 of polishing pad 1, the speed of rotation of substrate 5 about axis 14 of shaft 13, the speed of rotation of the polishing pad 1, the motor current used to power the motors used to rotate shaft 13 or the polishing pad 1, and the flow rate and composition of the polishing slurry used. Various system parameters and settings are available to control the polishing characteristics. It should be emphasized that the CMP operation and apparatus described above, are exemplary only. Various other system configurations are contemplated.

The CMP operation uses a polishing slurry to aid in the polishing operation. Inlet polishing slurry stream 19 is delivered to interface 9 along direction 21. The polishing slurry includes abrasive agents which aid the mechanical aspect of the CMP operation, and also a chemical component. When a metal film is being polished, an acidic polishing slurry is used. The acid within the acidic slurry reacts with the metal layer being polished and produces hydrogen vapor among its reaction products. The other reaction products produced from the reaction between the acid and the metal layer depend upon the metal being polished and the acid being used. The specific acid used, and the strength of the acid used, will depend upon the metal layer being polished and the specific polishing operation being carried out. Any suitable acid included in an acidic slurry, such as propionic acid, acetic acid, phosphoric acid or sulfuric acid, may be used. In an exemplary embodiment, when a copper-containing film is being polished by an acidic slurry including sulfuric acid, hydrogen vapor is produced according to the following exemplary chemical equation:

$$Cu + H_2SO_4 \rightarrow CuSO_4 + H_2\uparrow$$

It can be seen that $H_2$ vapor ($H_2\uparrow$) is produced during the reaction taking place between the acidic slurry and the metal layer.

Hydrogen sensor 15 which is connected to electronic circuit 17, is disposed at a location close to the interface 9 formed between substrate surface 7 which is being polished, and pad surface 3. Hydrogen sensor 15 is arranged in order to sense hydrogen vapor within product stream 20. In the exemplary embodiment shown in FIG. 3, polishing slurry stream 19 is introduced to interface 9 along direction 21, and is withdrawn along direction 22. Stated alternatively, the effluent slurry stream proceeds along direction 22. In this exemplary embodiment, hydrogen sensor 15 is located to sense hydrogen vapor within product stream 20 which includes the effluent slurry stream and is directed along direction 22. In other exemplary embodiments, hydrogen sensor 15 may be disposed at any location where it may sense hydrogen vapor produced during the reaction which occurs at the polishing surface, for example, in close proximity to interface 9 where the reaction is being carried out. Hydrogen sensor 15, along with electronic circuit 17 may be set up to detect hydrogen vapor by sampling on a periodic or continuous basis. The sampling period may be chosen based upon the expected time to attain endpoint.

The amount and concentration of hydrogen vapor being produced and contained within product stream 20 depends directly upon the amount of hydrogen vapor being produced as a result of the reaction between the acid within the acidic slurry and the metal material being removed by polishing. Therefore, when endpoint is attained and little or no metal material is available to react with the acidic polishing slurry, the concentration of $H_2$ vapor within product stream 20, will be diminished significantly.

Figure 4:
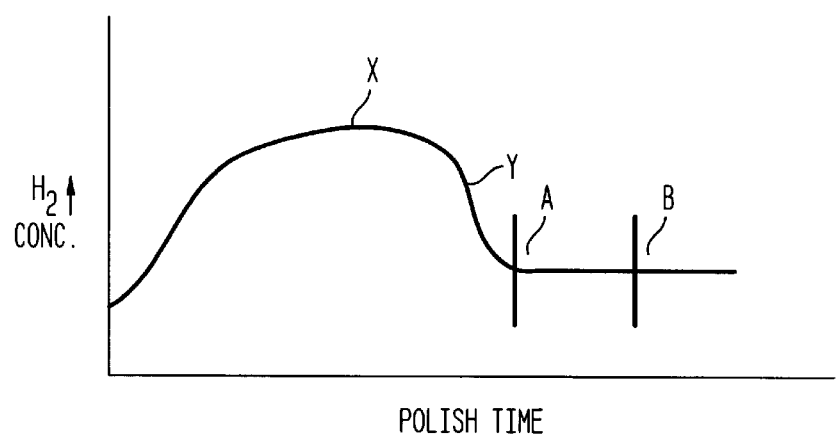
FIG. 4 is a graph showing a typical polishing endpoint curve.

FIG. 4 is a graph of a representative curve showing the concentration of $H_2$ vapor being produced as a function of polishing time. Such an $H_2$ concentration curve may be produced by hydrogen sensor 15 and electronic circuit 17 shown in FIG. 3. It can be seen that the sampling frequency is either essentially continuous, or that the sampling period was chosen to be small enough to produce a representative, continuous curve, from which an endpoint determination can be made. As the bulk of the metal film is being removed during the polishing operation, a maximum hydrogen concentration is achieved within the product stream and is indicated by point "X" on the curve. When the amount of hydrogen vapor being produced is reduced as endpoint approaches, the concentration of hydrogen vapor within the product stream drops. Section "Y" of the graph represents the portion of the polishing process, during which the last sections of the metal layer being polished, are removed. At inflection point "A", the curve has reached a minimum which continues on and remains substantially constant through point "B". Point "A" may generally be considered to be the point at which endpoint is attained. Depending on the polishing operation being performed, however, endpoint may be considered to be point "B" after a minimum value has been attained and remains constant for an arbitrary time as determined by the polishing operation. This determination may be made, in part, based on the desired amount of overetch. In response to the determination of endpoint at either point A or point B, action may be taken to adjust the polishing operation, as discussed above Hydrogen sensor 15 as shown in FIG. 3 may take on many forms. The hydrogen sensor 15 located in a position to sense hydrogen vapor being produced by the reaction occurring between the metal film and the acidic slurry, includes at least one sensing element. Various embodiments of sensing elements may be used, and the sensing element is oriented within the hydrogen sensor, to be exposed to the product stream or, more appropriately, to the hydrogen vapor. The sensing element includes a measurable characteristic which varies depending on the amount of hydrogen vapor present. Conventional electronic circuitry such as electronic circuit 17 may be used in conjunction with the hydrogen sensor 15, to measure the characteristic, and also to analyze and present the amount or concentration of hydrogen vapor detected based on the value of the measured characteristic. The data may be displayed in graphical, digital, or electronic form using conventional means.

A first exemplary embodiment of a hydrogen sensor may include a palladium gate MOS transistor as the sensing element. A palladium gate MOS transistor may be formed within a semiconductor substrate using conventional processing and having conventional dimensions. The palladium gate is arranged to be exposed to the hydrogen source. Hydrogen in the ambient environment outside the device, is adsorbed on the metal gate as atomic hydrogen dissolves in the metal and diffuses to the metal-oxide interface where it gives rise to a dipole layer. The dipole layer changes the work function difference between the metal and the semiconductor and thereby the threshold voltage of the MOS transistor. This threshold voltage change may be measured electrically using conventional means, such as electronic circuit 17. Such a hydrogen sensitive palladium gate MOS transistor is described in the article *A Hydrogen-Sensitive Pd-Gate MOS Transistor* by Lundström, Shivaraman and Svensson in Journal of Applied Physics, Vol. 46, No. 9, September 1975, pp. 3876–3881, which is being incorporated herein by reference. In this exemplary embodiment, when the hydrogen vapor concentration in the product stream changes, the threshold voltage of the palladium gate MOS transistor is the measurable characteristic which changes accordingly.

In a second exemplary embodiment, the sensing element may include an anodic tungsten oxide film to sense and indicate the presence of hydrogen vapor. In an exemplary embodiment, a film with the composition $WO_3.H_2O$ may be used. Also in an exemplary embodiment, a catalyst such as thin palladium film which adsorbs hydrogen atoms, may be formed over at least sections of the tungsten oxide film to act as a catalyst of sorts. When the anodic tungsten oxide film senses hydrogen vapor in the environment, both the coloration and conductivity of the film change in response to the hydrogen sensed. The change in conductivity or resistivity may be measured by electronic circuit 17 using conventional methods. The change in coloration produces a change in refractive index which can be noted visually, or measured electrically or optically using conventional techniques. For example, a conventional optical instrument may be used and oriented to measure the refractive index of the tungsten oxide film, which changes depending on the amount of hydrogen vapor present.

The technique for detecting hydrogen based on coloration changes, involves a hydrated, polycrystalline tungsten oxide film. The detector which is operative at room temperature, is formed, according to one exemplary embodiment, by forming a semi-transparent palladium over layer anodic oxide film tungsten sheet structure. The optical reflectance of the structure so formed, is modulated by the presence of hydrogen molecules in the ambient environment. The affect can be explained as follows. Hydrogen molecules are disassociated into hydrogen atoms on the palladium surface. The latter reducing species diffuses to form a tungsten blue phase in the tungsten oxide film. The coloration reaction causes an increase in free electron concentration, and therefore, a decrease in the refractive index, an increase in conductivity, and an increase in the extinction coefficient of the film. As above, a hydrated, anodic oxide film with the composition $WO_3 \cdot H_2O$ is used in the preferred embodiment. It is theorized that lattice water of this hydrate may assist rapid diffusion of the reducing species into the bulk of the film. Extensive modulation of the reflectance occurs when the film is thicker than 0.3 microns. The use of such a hydrogen detector based on coloration of an anodic tungsten oxide film is as described in the article *Hydrogen Detection Based on Coloration of Anodic Tungsten Oxide Film*, by Ito and Ohgami, in Applied Physics Letters, Vol. 60, No. 8, Feb. 24, 1992, pp. 938–940, which is hereby incorporated by reference.

A third exemplary embodiment of a sensing element which may be used to sense hydrogen in hydrogen sensor 15 of FIG. 3, may be industrial plastics which swell or expand in response to the presence of hydrogen vapor in the environment which they contact. When the expandable industrial plastic swells in response to the presence of hydrogen vapor, the electrical conductivity of the film changes. This electrical conductivity or resistivity may be measured by electronic circuit 17 using conventional techniques as commonly available in the art.

For each of the above-described embodiments of sensing elements, as the concentration of hydrogen vapor is being sensed by the sensing element as described above, conventional electronic circuitry may be used to measure the quantity of the characteristic of the sensing element, which varies with the amount of hydrogen present. Such characteristics may include, for example, the threshold voltage of the palladium gate MOS transistor or the conductivity/resistivity of the tungsten oxide film or expandable plastic. It should be understood that other is sensing elements which sense hydrogen vapor may be used alternatively. This conventional circuitry will also produce, analyze, and display a signal or other representation of the measured characteristic, which corresponds to the concentration of hydrogen vapor. A graphical display may be used as shown in FIG. 4, or a digital or other display may be used.

Once endpoint has been attained as indicated by a change in the graphical, digital, electrical, or other representation of hydrogen concentration in the product stream, a number of actions may be taken responsive to the endpoint condition being attained. An exemplary embodiment of such an action is to simply terminate the entire polishing process. Another exemplary response to endpoint condition being attained, may be to vary some or all of the characteristics of the polishing operation as described above by changing system parameters and settings. In this manner, a modified polishing operation continues. The modified polishing operation may be used to polish the underlying layer or layers. In one exemplary embodiment, the modified polishing operation may take the form of a buffing operation which smoothes the surface without significantly reducing the thickness. In another exemplary embodiment, additional conventional electronic circuitry (not shown) may be added to provide an electrical signal back to the polishing apparatus, which may automatically adjust the polishing operation.

The preceding description merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

As such, the invention is not intended to be limited to the details shown. Rather, various modifications and additions may be made in the details within the scope and range of equivalents of the claims and without departing from the invention.

What is claimed:

1. In a chemical mechanical polishing apparatus which uses a polishing slurry, an endpoint detector comprising a hydrogen vapor sensor mounted in the chemical mechanical polishing apparatus in close proximity to an interface formed between a polishing pad and a surface being polished and adapted for sensing hydrogen vapor produced as a reaction product during a chemical mechanical polishing operation.

2. The endpoint detector as in claim 1, further comprising an electronic circuit coupled to the hydrogen vapor sensor.

3. The endpoint detector as in claim 1, in which the hydrogen vapor sensor includes a sensing element oriented such that the sensing element is exposed to a product stream being withdrawn from the chemical mechanical polishing operation.

4. The endpoint detector as in claim 1, wherein the hydrogen vapor sensor includes a sensing element having a characteristic which changes depending on an amount of hydrogen vapor present, and further comprising an electronic circuit capable of measuring the characteristic.

5. The endpoint detector as in claim 1, wherein the hydrogen vapor sensor includes a palladium gate MOS transistor as a sensing element.

6. The endpoint detector as in claim 5, further comprising an electronic circuit capable of reading a threshold voltage of the transistor.

7. The endpoint detector as in claim 1, wherein the hydrogen vapor sensor includes, as a sensing element plastic which expands when exposed to hydrogen vapor.

8. The endpoint detector as in claim 7, wherein the plastic includes a conductivity which changes when the plastic expands, and further comprising an electronic circuit capable of measuring the conductivity.

9. The endpoint detector as in claim 7, further comprising means for sensing an expansion of the plastic.

10. The endpoint detector as in claim 1, wherein the hydrogen vapor sensor includes a tungsten oxide film structure as a sensing element.

11. The endpoint detector as in claim 10, further comprising a palladium layer disposed over the tungsten oxide film structure.

12. The endpoint detector as in claim 10, wherein the tungsten oxide film includes a conductivity which changes when hydrogen is adsorbed onto the tungsten oxide film, and further comprising an electronic circuit capable of measuring the conductivity.

13. The endpoint detector as in claim 11, in which the palladium layer is substantially transparent.

14. The endpoint detector as in claim 10, wherein the tungsten oxide film comprises a hydrated oxide film represented by $WO_3.H_2O$.

15. The endpoint detector as in claim 10, wherein the tungsten oxide film changes coloration when hydrogen is adsorbed onto the film, and further comprising an optical instrument capable of measuring a refractive index of the film.

16. In a chemical mechanical polishing apparatus which uses a polishing slurry, an endpoint detector comprising a hydrogen vapor sensor mounted in a chemical mechanical polishing apparatus in close proximity to a surface being polished, and adapted for sensing hydrogen vapor produced as a reaction product during a chemical mechanical polishing operation, and an electronic circuit coupled to the hydrogen vapor sensor.

17. The endpoint detector as in claim 16, wherein the hydrogen vapor sensor includes a sensing element having a characteristic which changes depending on an amount of hydrogen vapor present, and the electronic circuit is capable of measuring the characteristic.

18. The endpoint detector as in claim 17, wherein the sensing element comprises a tungsten oxide film and the characteristic comprises conductivity.

* * * * *